United States Patent [19]

Bloch

[11] 4,104,370
[45] Aug. 1, 1978

[54] METHOD OF TREATING MAGNESIUM/POTASSIUM DEPLETION

[75] Inventor: Maurice Bloch, London, England

[73] Assignee: Smith Kline & French Laboratories Limited, Welwyn Garden City, England

[21] Appl. No.: 633,210

[22] Filed: Nov. 19, 1975

Related U.S. Application Data

[63] Continuation-in-part of Ser. No. 487,117, Jul. 10, 1974, abandoned.

[51] Int. Cl.$^2$ ............... A61K 33/14; A61K 33/06; A61K 9/22; A61K 9/24
[52] U.S. Cl. ........................ 424/153; 424/154; 424/19; 424/21
[58] Field of Search ............ 424/153, 154, 156, 157, 424/19, 21

[56] References Cited

U.S. PATENT DOCUMENTS

| | | | |
|---|---|---|---|
| 2,224,252 | 12/1940 | Callaway | 99/1 |
| 3,337,404 | 8/1967 | Polli et al. | 424/153 |
| 3,356,570 | 12/1967 | Butcher | 424/153 |
| 3,676,553 | 7/1972 | Reynolds | 424/153 |

OTHER PUBLICATIONS

The Pharmaceutical Journal, Dec. 13, 1952, vol. 169, p. 418.
Levowitz, et al., Surgical Forum, vol. 18, 315–317, (1967).
Levowitz, et al., Surgery, Gynecology and Obstetrics, 129: 979–988 (1969).

*Primary Examiner*—Albert T. Meyers
*Assistant Examiner*—Daren M. Stephens
*Attorney, Agent, or Firm*—Joan S. Keps; Richard D. Foggio; William H. Edgerton

[57] ABSTRACT

A method of treating magnesium/potassium depletion which comprises administering pharmaceutical compositions comprising magnesium and potassium compounds, the equivalent weight of the magnesium being between 1 and 3 times the equivalent weight of the potassium, together with a pharmaceutical carrier such that the rate of release of the magnesium and potassium into the digestive system is controlled.

8 Claims, No Drawings

METHOD OF TREATING MAGNESIUM/POTASSIUM DEPLETION

This application is a continuation-in-part of Ser. No. 487,117 filed Jul. 10, 1974, now abandoned.

This invention relates to methods of treating magnesium/potassium depletion by administering pharmaceutical compositions comprising magnesium and potassium compounds. Also, this invention relates to new pharmaceutical compositions comprising magnesium and potassium compounds in combination with a diuretic or cardiac glycoside.

With the more ready availability of atomic absorption spectroscopy for determination of the magnesium content of tissues there is, at present, an increasing interest in the diagnosis and treatment of magnesium depletion such as might occur in association with alcoholism, diabetes mellitus, the use of diuretics, etc. This depletion results in secondary potassium depletion, the intracellular concentrations of magnesium and potassium ions being inter-related. Potassium ions as well as magnesium ions should therefore be given to patients. However, in addition to the problems which can arise when magnesium is administered owing to its purgative actions, when potassium is also given other unwanted side-effects e.g. vasoconstriction and gastric ulceration, may occur.

It is one of the objects of the present invention to provide a novel method for the administration of magnesium together with potassium whilst reducing these unwanted side-effects.

Vasoconstrictor activity of potassium ions may contribute to diminished and/or delayed absorption of the compound, and might contribute to local mucosal ulceration of the gut. This action can be prevented by magnesium ions, which have vasodilator activity, provided the concentration of magnesium (m.eq./l.) exceeds that of the potassium ions.

Therapeutic usefulness of magnesium might be limited also by its purgative action on the gut, unless administered in comparatively small doses. This limitation might be overcome with the use of a slow-release preparation so that magnesium might be administered in therapeutically meaningful dosages in the treatment of magnesium depletion.

Thus by attention to rate of release of the compound within the gut, and by attention to the ratio of magnesium to potassium in the compound, the principal complications resulting from the use of a magnesium-potassium or magnesium-calcium-potassium compound, namely, delayed absorption, mucosal ulceration and purgation, may be avoided. Such a preparation would be suitable for use in the treatment of magnesium/potassium depletion states.

According to the present invention, there is provided a method of treating magnesium/potassium depletion in humans by administering orally a pharmaceutical composition, in solid form for oral administration, comprising magnesium oxide, magnesium hydroxide, or a non-toxic pharmaceutically acceptable salt of magnesium in combination with a non-toxic pharmaceutically acceptable salt of potassium, the equivalent weight of the magnesium being between 1 and 3, and preferably between 1 and 2, times the equivalent weight of the potassium, together with a pharmaceutical carrier such that the rate of release of the magnesium and potassium into the digestive system is controlled. Within the phrase 'treatment of magnesium/potassium depletion' we mean to include not only the treatment of patients already suffering from such depletion, but also prophylactic treatment.

Preferably the magnesium is in the form of magnesium oxide, magnesium hydroxide, magnesium chloride, magnesium sulphate, magnesium gluconate or magnesium phosphate or a combination of these compounds. In some cases however, magnesium carbonate may be employed. Because of its high magnesium content it is found that magnesium oxide is particularly useful.

The potassium is preferably in the form of potassium chloride. The amount of potassium and magnesium salts to be incorporated in the composition will of course be related to the dosage which it is required to administer to the patient and the length of time over which the salts will be released from the carrier. The daily dosage required will normally be in the range of from 10 to 30 milliequivalents (m.eq.) of magnesium and from 10 to 25 m.eq. of potassium and a convenient length of time of action for a sustained release composition is from 2 to 8 hours. Thus it will be evident that the compositions will preferably contain from 2 to 15 m.eq. of magnesium and from 2 to 10 m.eq. of potassium. Particularly useful compositions are those which contain from 3 to 7 m.eq. of magnesium and from 2 to 5 m.eq. of potassium.

Any suitable controlled or sustained release formulation may be used in the preparation of the compositions in order to obtain the required controlled rate of release in the digestive system. One type of such preparation is based on a plurality of small cores which may be themselves of an inactive material such as sugar, synthetic resin or naturally occuring seeds such as rape seeds. Particularly suitable are "nonpareil seeds" as used in the confectionery industry which comprise sugar crystals coated with starch, talc, kaolin and syrup. This method is disclosed in U.S. Pat. No. 2,738,303. Alternatively, the cores may themselves be formed of the medicament to be administered, as described in U.S. Pat. No. 3,119,742, i.e. in the case of the present invention of a potassium and/or magnesium compound. These cores are then coated with one or more layers of a material which dissolves at a slow but controlled rate in the gastro-intestinal tract of the patient. Examples of such time-delay materials (which are described in greater detail hereinafter) include glyceryl monostearate and beeswax and since the latter is much less dispersible than the former, by varying the relative amounts of these materials the rate of dissolution and so the rate of release of the medicament (which may be incorporated within the coating material, form the central core or be applied as a separate layer between the core and the coating material) can be controlled. The rate of release may also be varied by altering the thickness of the coating material applied. A plurality of coated cores are combined in a suitable form such as a capsule, a tablet (a binder may be required in this case) or a suspension in a liquid. By combining coated cores having different time release characteristics a continuing release of medicament over a period of many hours from administration may be achieved. It will be understood that, by including uncoated medicament in the composition, an immediate effect can also be attained. The rate of absorption of the medicament used is a further factor which must be considered, and medicaments which are absorbed slowly generally only require a thin protective coating.

Another type of controlled release formulation which may be used is that which is produced by a process involving microencapsulation techniques.

Other well known methods of preparing sustained release preparations may also be employed. For example, the magnesium and potassium compounds may be dispersed in a molten wax and then spray congealed as disclosed in U.S. Pat. No. 3,146,167. Fine powders comprising the magnesium and potassium compounds may be suspended in a tower and coated with time delay material, as described in U.S. Pat. No. 3,411,480. Those coated powders can then be suspended in a liquid or encapsulated. Sustained release granules may also be prepared as disclosed in U.S. Pat. No. 3,108,046 and either tabletted or placed in a soft gelatine capsule. Sustained release layered tablets may be prepared as described in U.S. Pat. No. 2,951,792.

The time delay material is a substantially water insoluble material resistant to disintegration in the gastrointestinal tract and providing for a gradual release of the medicament in said tract. The time delay material may be, for example, a wax, a fatty acid, alcohol or ester, alone, or an admixture thereof.

The wax may be paraffin wax; a petrolatum wax; a mineral wax such as ozokerite, ceresin, utah wax or montan wax; a vegetable wax such as, for example, carnauba wax, Japan wax, bayberry wax, flax wax; an animal wax such as, for example, spermaceti; or an insect wax such as beeswax, Chinese wax or shellac wax. Additionally, the wax material may be an ester of a fatty acid having from 12 to 31 carbon atoms and a fatty alcohol having from 12 to 31 carbon atoms, the ester having a carbon atom content of from 24 to 62, or a mixture thereof. Exemplary are myricyl palmitate, ceryl palmitate, ceryl cerotate, myricyl mellissate, stearyl palmitate, stearyl myristate, lauryl laurate.

The fatty acid may have from 10 to 22 carbon atoms and may be for example, decenoic, docosanoic, stearic, palmitic, lauric or myristic acid.

The fatty alcohols may have from 10 to 36 carbon atoms and may be, for example, lauryl alcohol, cetyl, stearyl, myristyl, myricyl, arachyl, carnaubyl or ceryl alcohol.

The esters may be mono-, di- or triglyceryl esters formed from fatty acids having from 10 to 22 carbon atoms, such as, for example, glyceryl distearate, glyceryl tristearate, glyceryl monostearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate, glyceryl tridecenoate, hydrogenated castor oil, hydrogenated peanut oil and hydrogenated coconut oil.

The preferred sustained release materials are hydrogenated castor oil, glyceryl monostearate, glyceryl distearate, 12-hydroxystearyl alcohol and microcystalline wax.

Other pharmaceutically acceptable substances may be included in the above described compositions. For example, a diuretic or a cardiac glycoside may be combined with the magnesium/potassium compositions described hereabove to form pharmaceutical compositions which are further objects of this invention. Exemplary of diuretics in the compositions of this invention are mercurial diuretics such as chlormerodrin; carbonic anhydrase inhibitors for example acetazolamide; benzothiadiazides for example bendroflumethiazide, benzthiazide, hydrochlorothiazide, chlorothiazide, cyclopenthiazide and altizide; benzenesulfonamides for example, furosemide, mefruside, bumetanide clopamide and chlorthalidone; ethacryic acid; and ticrynafen. Exemplary of cardiac glycosides in the compositions of this invention are digoxin, digitoxin and lanatoside C. The diuretic agents and cardiac glycosides are present in amounts effective to produce the diuretic and cardiotonic activity. The effective amounts of the above mentioned diuretics and cardiac glycosides are known to the art. The appropriate daily dose of diuretic agent and cardiac glycoside may be equally divided between an appropriate number of tablets or capsules, or the daily dose may be equally divided between from one to three tablets or capsules and the latter tablets or capsules may be administered in conjunction with tablets or capsules containing only a magnesium/potassium composition. The diuretic agent and cardiac glycoside may be present in the pharmaceutical formulation with or without means for controlling their release into the digestive system.

The invention is illustrated but in no way limited by the following specific examples:

EXAMPLE 1

A mixture of magnesium oxide, a flowing agent such as fumed silicon dioxide, a disintegrant such as an alginate and starch or another pharmaceutical excipient to aid in disintegration and dispersion is milled and added to a tacky suspension of nonpareil seeds in an adhesive mixture comprising polyvinylpyrrolidone and a wetting agent dissolved in methylated spirits. When no more of the milled powder will adhere to the seeds, the coated pellets are dried by a stream of air and a further layer of coating applied by the same method. Finally a protective coating of glycerol monostearate/beeswax is applied to the pellets which now have a diameter of approximately 1 mm.

By similar means milled potassium chloride is coated on to nonpareil seeds and covered with a protective and delayed release coating.

The two types of pellets are mixed and filled into No. 0 capsules in such proportions that each capsule contains 100 mg (5 milliequivalents) of magnesium oxide and 300 mg (4 milliequivalents) of potassium chloride.

EXAMPLE 2

Pellets containing magnesium oxide and pellets containing potassium chloride described in Example 1 are mixed and filled into No. 0 capsules in such proportions that each capsule contains 120 mg (6 milliequivalents) of Magnesium Oxide and 225 mg (3 milliequivalents) of potassium chloride.

EXAMPLE 3

(a) A mixture of furosemide and a disintegrant such as starch is milled and added to a tacky suspension of nonpareil seeds in an adhesive mixture comprising gelatine in aqueous ethanol. When no more of the milled powder will adhere to the seeds, the coated pellets are dried by a stream of air and a further layer of coating applied by the same method. Finally a very thin coating of glycerol monostearate/beeswax is applied to the pellets.

(b) These pellets containing furosemide are mixed with pellets containing magnesium oxide and pellets containing potassium chloride described in Example 1 and filled into No. 0 capsules in such proportions that each capsule contains 20 mg furosemide, 96 mg (4.8 m.eq.) magnesium oxide and 180 mg (2.4 m.eq.) potassium chloride.

EXAMPLE 4

Pellets containing
(a) hydroflumethiazide
(b) mefruside
(c) chlorthalidone
(d) clopamide
(e) hydrochlorothiazide
(f) methylclothiazide
(g) bendrofluazide
(h) bumetanide
(i) cyclopenthiazide
are prepared by substituting the above compounds for furosemide in the procedure of Example 3a and these pellets are mixed with pellets containing magnesium oxide and pellets containing potassium chloride described in Example 1 and filled into No. 0 capsules in such proportions that the capsules contain 96 mg (4.8 m.eq.) magnesium oxide, 180 mg (2.4 m.eq.) potassium chloride and
(a) 25 mg hydroflumethiazide
(b) 25 mg mefruside
(c) 25 mg chlorthalidone
(d) 20 mg clopamide
(e) 12.5 mg hydrochlorothiazide
(f) 5 mg methylclothiazide
(g) 2.5 mg bendrofluazide
(h) 1 mg bumetanide
(i) 0.25 mg cyclopenthiazide

EXAMPLE 5

Nonpareil seeds are coated with a mixture of digoxin and polyvinylpyrolidone in ethanol, and the coated pellets are dried by a stream of air.

These pellets are mixed with pellets containing magnesium oxide and pellets containing potassium chloride described in Example 1 and filled into No. 0 capsules in such proportions that each capsule contains 0.125 mg digoxin, 96 mg (4.8 m.eq.) magnesium oxide and 180 mg (2.4 m.eq.) potassium chloride.

EXAMPLE 6

Ticrynafen is mixed with talc and stearic acid. Gelatin in water is added and the mixture is granulated by passing through a screen and the mixture is dried and screened. Another granulation is prepared by adding potassium chloride to molten hydrogenated castor oil, stirring the mixture until cool, and passing the congealed product through a cominution mill and screen.

A third granulation is prepared by adding magnesium oxide to molten hydrogenated castor oil, stirring the mixture until cool, and passing the congealed product through a cominution mill and screen.

The three types of granules are compressed to form three-layer cylindrical flat-faced tablets each comprising 125 mg ticrynafen, 120 mg magnesium oxide and 225 mg potassium chloride.

I claim:

1. A method of treating magnesium/potassium depletion without the unwanted purgative action of magnesium in a human requiring such treatment which comprises administering orally to said human a pharmaceutical composition, in an effective amount of the composition to produce said activity, in solid form for oral administration in a sustained release capsule or layered tablet, comprising magnesium oxide, magnesium hydroxide or a non-toxic pharmaceutically acceptable salt of magnesium in combination with potassium chloride, the equivalent weight of the magnesium being between 1 and 3 times the equivalent weight of the potassium, together with a pharmaceutical carrier such that the rate of release of the magnesium and potassium into the digestive system is controlled so that the length of time of action of said composition is from 2 to 8 hours.

2. A method according to claim 1 in which the equivalent weight of the magnesium is about twice the equivalent weight of the potassium.

3. A method according to claim 1 in which the magnesium is in the form of magnesium oxide, magnesium hydroxide, magnesium chloride, magnesium sulphate, magnesium gluconate or magnesium phosphate.

4. A method according to claim 3 in which the magnesium is in the form of magnesium oxide.

5. A method according to claim 1 in which all of the magnesium and potassium is coated such that the rates of release into the digestive system may be controlled.

6. A method according to claim 1 in which in the pharmaceutical composition the amount of magnesium is from 2 to 15 milligram equivalents and the amount of potassium is from 2 to 10 milligram equivalents.

7. A method according to claim 1 in which in the pharmaceutical composition the amount of magnesium is from 3 to 7 milligram equivalents and the amount of potassium is from 2 to 5 milligram equivalents.

8. A method of claim 1 in which the pharmaceutical composition consists essentially of magnesium oxide, magnesium hydroxide or a non-toxic pharmaceutically acceptable salt of magnesium in combination with potassium chloride.

* * * * *